United States Patent
Fukami et al.

[11] Patent Number: 6,166,038
[45] Date of Patent: Dec. 26, 2000

[54] AMINOPYRAZOLE DERIVATIVES

[75] Inventors: Takehiro Fukami; Takahiro Fukuroda; Akio Kanatani; Masaki Ihara, all of Tsukuba, Japan

[73] Assignee: Banyu Pharmaceutical Co., Ltd., Tokyo, Japan

[21] Appl. No.: 09/319,270

[22] PCT Filed: Dec. 12, 1997

[86] PCT No.: PCT/JP97/04571
§ 371 Date: Jul. 30, 1999
§ 102(e) Date: Jul. 30, 1999

[87] PCT Pub. No.: WO98/25908
PCT Pub. Date: Jun. 18, 1998

[30] Foreign Application Priority Data

Dec. 13, 1996 [JP] Japan .................................. 8-353077

[51] Int. Cl.⁷ .................... A61K 31/445; A61K 31/415; C07D 401/12; C07D 231/38

[52] U.S. Cl. ................. 514/326; 546/211; 548/364.1; 548/371.4; 548/372.5; 514/407; 514/212; 514/183; 544/480; 544/603

[58] Field of Search ..................... 514/326, 407, 514/212, 183; 546/211; 548/364.1, 371.4, 372.5, 375.1; 544/480, 603

[56] References Cited

U.S. PATENT DOCUMENTS 4,089,962  5/1978  Harrison ................... 424/269

FOREIGN PATENT DOCUMENTS 51-146465  12/1976  Japan .
2-300173  12/1990  Japan .
3-93774   4/1991   Japan .
WO 96/14843  5/1996  WIPO .
WO 99/27965  6/1999  WIPO .

*Primary Examiner*—Charanjit S. Aulakh
*Attorney, Agent, or Firm*—Oblon, Spivak, McClelland, Maier & Neustadt, P.C.

[57] ABSTRACT

The present invention relates to a compound represented by the general formula [I]:

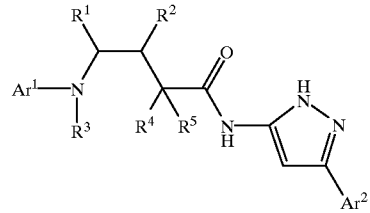

wherein $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ and $R^2$ may be the same or different and each represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a lower alkyl or lower alkoxy group, or its salt, a method for its preparation as well as an agent for the treatment of bulimia, obesity or diabetes comprising it as an active ingredient.

11 Claims, No Drawings

AMINOPYRAZOLE DERIVATIVES

This application is a 371 of PCT/JP97/04571 filed Dec. 12, 1997, now WO 98/25908 Jun. 18, 1998

FIELD OF THE INVENTION

The present invention is useful in the field of medicines. More specifically, novel pyrazole derivatives of the present invention are useful as neuropeptide Y receptor antagonists and as agents for the treatment of various diseases of circulatory organs, central nervous system and metabolic system.

BACKGROUND OF THE INVENTION

Neuropeptide Y. (to be referred to as NPY hereinafter) is a peptide consisting of 36 amino acids, which was isolated from porcine brain for the first time by Tatemoto et al. in 1982 [Nature, vol.296, p.659 (1982)]. NPY is broadly distributed in central and peripheral nervous systems and has various in vivo functions as one of the peptides most abundantly present in the nervous system. That is, in the central nervous system, NPY acts as an aperitive and significantly promotes a fat accumulation via secretion of various hormones and actions of the nervous system. It is known that a continuous intracerebroventricular administration of NPY induces obesity and insulin resistance based on the above actions. NPY is also associated with the control of mood and functions of the central autonomic nervous system. In addition, in the peripheral nervous system, NPY is present together with norepinephrine in the sympathetic nerve terminal and associated with the tension of the sympathetic nervous system. It is known that a peripheral administration of NPY causes vasoconstriction and enhances actions of other vasoconstrictors including norepinephrine [International Journal of Obesity, vol.19, p.517 (1995); Endocrinology, vol.133, p.1753 (1993); British Journal of Pharmacology, vol.95, p.419 (1988)].

The function of NPY is expressed when it is bound to an NPY receptor present in the central or peripheral nervous system. Therefore, the expression of the function of NPY can be prevented if the binding of NPY to the NPY receptor is inhibited. Consequently, it is expected that compounds capable of inhibiting the binding of NPY to the NPY receptor are useful in the prevention or treatment of various diseases associated with NPY, for example, diseases of circulatory organs such as hypertension, nephropathy, cardiopathy and angiospasm; diseases of central nervous system such as bulimia, depression, epilepsy and dementia; metabolic diseases such as obesity, diabetes and dysendocrisiasis; or glaucoma [Trends in Pharmacological Sciences, vol.15, p.153 (1994)].

Compounds structurally similar to the compounds of the present invention are disclosed in International Publication WO 96/14843, JP 3093774A, JP 2300173A, JP 51146465A and etc. However, these publications do not clearly disclose nor suggest the compound of the present invention. And, an antagonistic action to NPY is not described at all therein.

DISCLOSURE OF THE INVENTION

An object of the present invention is to provide a new medicine having an antagonistic action to NPY.

The present inventors found that a compound represented by the general formula [I]:

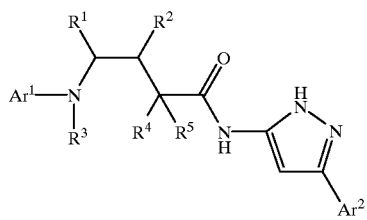

wherein $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ and $R^2$ may be the same or different and each represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a lower alkyl or lower alkoxy group,
has an antagonistic action to NPY.

Since the compound [I] of the present invention has the antagonistic action to NPY, it is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma.

Especially, the compound [I] of the present invention is useful as an agent for the treatment of bulimia, obesity, diabetes or the like.

The present invention relates to a compound represented by the general formula [I] or its salt as well as a method for its preparation and its use.

Symbols and terms as used herein are described below.

The term "halogen atom" as used herein means fluorine, chlorine, bromine or iodine.

The term "lower alkyl group" as used herein means a straight, branched or cyclic alkyl group containing 1 to 7 carbon atoms, and its illustrative examples include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, cyclopropyl, cyclobutyl, cyclopentyl, cyclohexyl, cycloheptyl, cyclopropylmethyl, 1-cyclopropylethyl, 2-cyclopropylethyl, 1-cyclopropylpropyl, 2-cyclopropylpropyl, 3-cyclopropylpropyl, cyclopentylmethyl, 2-cyclopentylethyl and cyclohexylmethyl and the like.

The term "lower haloalkyl group" as used herein means the above lower alkyl group comprising the aforementioned halogen atom, and its illustrative examples include fluoromethyl, difluoromethyl, trifluoromethyl, 1-fluoroethyl, 2-fluoroethyl, 2,2,2-trifluoroethyl, pentafluoroethyl, chloromethyl, dichloromethyl, trichloromethyl, 1-chloroethyl and 2-chloroethyl and the like.

The term "aryl group" as used herein means phenyl, naphthyl or anthryl, of which phenyl and naphthyl are preferred.

The term "lower alkenyl group" as used herein means a straight or branched alkenyl group containing 2 to 7 carbon atoms, and its illustrative examples include vinyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl and the like.

The term "lower alkoxy group" as used herein means an alkoxy group comprising the aforementioned lower alkyl group, namely an alkoxy group containing 1 to 7 carbon atoms, or an alkylenedioxy group containing 1 to 3 carbon atoms, and its illustrative examples include methoxy, ethoxy, propyloxy, isopropyloxy, butoxy, isobutyloxy, tert-butoxy, pentyloxy, cyclopropyloxy, cyclobutyloxy, cyclopentyloxy, cyclohexyloxy, cycloheptyloxy, cyclopropylmethyloxy, 1-cyclopropylethyloxy, 2-cyclopropylethyloxy, 1-cyclopropylpropyloxy, 2-cyclopropylpropyloxy, 3-cyclopropylpropyloxy, cyclopentylmethyloxy, 2-cyclopentylethyloxy, cyclohexylmethyloxy, methylenedioxy, ethylenedioxy and trimethylenedioxy and the like.

The term "lower alkylthio group" as used herein means an alkylthio group comprising the aforementioned lower alkyl group, namely an alkylthio group containing 1 to 7 carbon atoms, and its illustrative examples include methylthio, ethylthio, propylthio, isopropylthio, butylthio, isobutylthio, tert-butylthio, pentylthio, cyclopropylthio, cyclobutylthio, cyclopentylthio, cyclohexylthio, cycloheptylthio, cyclopropylmethylthio, 1-cyclopropylethylthio, 2-cyclopropylethylthio, 1-cyclopropylpropylthio, 2-cyclopropylpropylthio, 3-cyclopropylpropylthio, cyclopentylmethylthio, 2-cyclopentylethylthio and cyclohexylmethylthio and the like.

The term "lower alkylamino group" as used herein means an amino group monosubstituted with the aforementioned lower alkyl group, and its illustrative examples include methylamino, ethylamino, propylamino, isopropylamino, butylamino, sec-butylamino and tert-butylamino and the like.

The term "lower dialkylamino group" as used herein means an amino group disubstituted with the aforementioned lower alkyl group, and its illustrative examples include dimethylamino, diethylamino, ethylmethylamino, dipropylamino, methylpropylamino and diisopropylamino and the like.

The term "heteroaryl group" as used herein means a 5- or 6-membered monocyclic aromatic heterocyclic ring group containing 1 or more, preferably 1 to 3, of heteroatoms which may be the same or different and are selected from the group consisting of oxygen, nitrogen and sulfur, or a condensed aromatic heterocyclic ring group in which said monocyclic aromatic heterocyclic ring group and the aforementioned aryl group are condensed or in which the same or different members of said monocyclic aromatic heterocyclic ring groups are mutually condensed, and its illustrative examples include pyrrolyl, furyl, thienyl, imidazolyl, pyrazolyl, thiazolyl, isothiazolyl, oxazolyl, isoxazolyl, triazolyl, oxadiazolyl, thiadiazolyl, pyridyl, pyrazinyl, pyrimidinyl, pyridazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl and pteridinyl and the like.

The term "alkylene group containing 2 to 4 carbon atoms" as used herein means a straight chain alkylene group, namely ethylene, trimethylene or tetramethylene.

The "salt" of the compound represented by the general formula [I] means any conventional pharmaceutically acceptable salt, and its examples include acid addition salts based on basic groups such as a basic heterocyclic ring group or an amino substituent and the like.

Illustrative examples of the acid addition salt include an inorganic salt such as hydrochloride, sulfate, nitrate, phosphate and perchlorate; an organic salt such as maleate, fumarate, tartarate, citrate, ascorbate and trifluoroacetate; and sulfonate such as methanesulfonate, isethionate, benzenesulfonate and p-toluenesulfonate.

The term "agent for the treatment" as used herein means a drug to be used for the treatment and/or prevention of various diseases.

Various symbols used in the general formula [I] are described further in detail with reference to its preferred embodiment in order to explain the compound represented by the general formula [I] of the present invention more clearly.

$Ar^1$ means an aryl group which may have a substituent selected from the group consisting of a halogen atom and lower alkyl and lower haloalkyl groups.

The term "an aryl group which may have a substituent selected from the group consisting of a halogen atom and lower alkyl and lower haloalkyl groups" means the aforementioned aryl group unsubstituted or substituted at any substitutable position with 1 or more, preferably 1 or 2, substituents which may be the same or different and are selected from the group consisting of a halogen atom and lower alkyl and lower haloalkyl groups.

Preferred examples of the halogen atom as said substituent include chlorine and bromine.

Preferred examples of the lower alkyl group as said substituent include methyl, ethyl, propyl, isopropyl, cyclopropyl, butyl, isobutyl, sec-butyl, tert-butyl and pentyl, of which methyl, ethyl, propyl, isopropyl and cyclopropyl are more preferred.

Preferred examples of the lower haloalkyl group as said substituent include trifluoromethyl.

A halogen atom is preferred as said substituent.

Preferred examples of the aryl group as $Ar^1$ include phenyl.

In consequence, preferred examples of $Ar^1$ include phenyl and 3-chlorophenyl, of which 3-chlorophenyl is more preferred.

$Ar^2$ means an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups.

The term "an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups" means the aforementioned aryl or heteroaryl group unsubstituted or substituted at any substitutable position with 1 or more, preferably 1 or 2, substituents which may be the same or different and are selected from the group consisting of a halogen atom and lower alkyl, lower alkenyl, lower haloalkyl, lower alkoxy, lower alkylthio, lower alkylamino, lower dialkylamino and aryl groups.

Preferred examples of the halogen atom as said substituent include chlorine and bromine.

Preferred examples of the lower alkyl group as said substituent include methyl and ethyl.

Preferred examples of the lower alkenyl group as said substituent include vinyl, 2-propenyl, isopropenyl, 2-butenyl and 3-methyl-2-butenyl, of which vinyl and 2-propenyl are more preferred.

Preferred examples of the lower haloalkyl group as said substituent include fluoromethyl and trifluoromethyl.

Preferred examples of the lower alkoxy group as said substituent include methoxy, ethoxy, propyloxy and methylenedioxy, of which methoxy and methylenedioxy are more desirable.

Preferred examples of the lower alkylthio group as said substituent include methylthio, ethylthio and propylthio, of which methylthio is more preferred.

Preferred examples of the lower alkylamino group as said substituent include methylamino.

Preferred examples of the lower dialkylamino group as said substituent include dimethylamino.

Preferred examples of the aryl group as said substituent include phenyl.

As said substituent, a halogen atom and a lower alkyl, lower alkoxy, lower alkylthio or lower dialkylamino group are more preferred.

Preferred examples of the aryl group as $Ar^2$ include phenyl, and those of the heteroaryl group include pyridyl.

In consequence, preferred examples of $Ar^2$ include phenyl, 1-naphthyl, 2-naphthyl, 2-pyridyl, 3-pyridyl, 4-pyridyl, 2-chlorophenyl, 3-chlorophenyl, 4-chlorophenyl, 3,4-dichlorophenyl, 2-bromophenyl, 3-bromophenyl, 4-bromophenyl, 5-chloro-3-pyridyl, 5-bromo-3-pyridyl, 2-methylphenyl, 3-methylphenyl, 4-methylphenyl, 3-ethylphenyl, 4-ethylphenyl, 4-propylphenyl, 5-methyl-2-pyridyl, 6-methyl-3-pyridyl, 6-ethyl-3-pyridyl, 2-methyl-4-pyridyl, 2-ethyl-4-pyridyl, 2-propyl-4-pyridyl, 2-butyl-4-pyridyl, 3-methyl-4-pyridyl, 3-vinylphenyl, 4-vinylphenyl, 4-(2-propenyl)phenyl, 5-vinyl-3-pyridyl, 3-trifluoromethylphenyl, 4-trifluoromethylphenyl, 2-methoxyphenyl, 3-methoxyphenyl, 4-methoxyphenyl, 4-ethoxyphenyl, 4-isopropyloxyphenyl, 3,4-dimethoxyphenyl, 3,4-methylenedioxyphenyl, 6-methoxy-3-pyridyl, 2-methoxy-4-pyridyl, 3-dimethylaminophenyl, 4-dimethylaminophenyl, 4-methoxy-3-dimethylaminophenyl, 2-methylthiophenyl, 3-methylthiophenyl, 4-methylthiophenyl, 2-methylthio-4-pyridyl, 3-biphenylyl and 4-biphenylyl, of which 4-pyridyl, 2-methyl-4-pyridyl, 2-ethyl-4-pyridyl, 2-propyl-4-pyridyl, 2-butyl-4-pyridyl, 3-chlorophenyl, 4-chlorophenyl, 3,4-dichlorophenyl, 3-bromophenyl, 4-bromophenyl, 2-methylphenyl, 3-methylphenyl, 4-methylphenyl, 4-ethylphenyl, 3-methyl-4-pyridyl, 3-ethyl-4-pyridyl, 4-vinylphenyl, 4-(2-propenyl)phenyl, 3-methoxyphenyl, 4-methoxyphenyl, 4-ethoxyphenyl, 3,4-dimethoxyphenyl, 3,4-methylenedioxyphenyl, 3-methoxy-4-pyridyl, 4-methylthiophenyl and 3-methylthio-4-pyridyl are more preferred.

$R^1$ and $R^2$ may be the same or different and each means a hydrogen atom or a lower alkyl group.

Preferred examples of the lower alkyl group as $R^1$ and $R^2$ include methyl and ethyl.

Hydrogen atom is preferred as both of the $R^1$ and $R^2$.

$R^3$ and $R^4$ may be the same or different from each other and each means a hydrogen atom or a lower alkyl group or an alkylene group containing 2 to 4 carbon atoms which is formed by linking $R^3$ and $R^4$ and which may have a lower alkyl group.

Preferred examples of the lower alkyl group as $R^3$ and $R^4$ include methyl and ethyl.

The term "an alkylene group containing 2 to 4 carbon atoms which may have a lower alkyl group" means the aforementioned alkylene group unsubstituted or substituted at any substitutable position with 1 or more of the aforementioned lower alkyl groups which may be the same or different. The unsubstituted alkylene group is preferred.

Preferred examples of the lower alkyl group as the substituent include methyl, ethyl, propyl and isopropyl, of which methyl is more preferred.

Preferred examples of $R^3$ and $R^4$ include a lower alkyl group which may be the same or different, and an alkylene group containing 2 to 4, particularly 2, carbon atoms which is formed by linking $R^3$ and $R^4$ and which may have a lower alkyl group.

$R^5$ means a hydrogen atom or a lower alkyl or lower alkoxy group.

Preferred examples of the lower alkyl group as $R^5$ include methyl and ethyl.

Preferred examples of the lower alkoxy group as $R^5$ include an alkoxy group containing 1 to 7 carbon atoms such as methoxy, ethoxy and propyloxy, of which methoxy is more preferred.

Preferred as $R^5$ is hydrogen.

Depending on the nature of substituent, the compounds of the present invention may exists in various stereoisomers including optical isomers, diasteromers and geometrical isomers, and tautomers.

All of these stereoisomers and tautomers and their mixtures are also included in the present invention.

In this connection, in order to avoid unnecessary confusion in naming each of the compounds of the present invention, position numbers of the pyrazole ring moiety of the compound represented by the general formula [I] are defined as shown in the following general formula [I'], and the nomenclature and other explanations of each compound are described based on this formula.

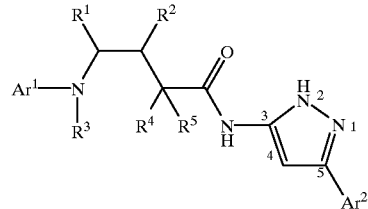

[I']

Illustrative examples of the compound represented by the general formula [I] include:

5-(4-chlorophenyl)-3-(1-phenylpiperidin-4-yl) carbonylaminopyrazole, 5-(4-methoxyphenyl)-3-(1-phenylpiperidin-4-yl) carbonylaminopyrazole, 5-(3,4-dichlorophenyl)-3-(1-phenylpiperidin-4-yl) carbonylaminopyrazole, 3-[1-(3-chlorophenyl)piperidin-4-yl]carbonylamino-5-(4-methoxyphenyl)pyrazole.

Next, processes for the preparation of the compound of the present invention are described below.

The compound represented by the general formula [I] can be prepared, for example, by one of the following processes or the methods as shown in examples, provided that the process for the preparation of the compound [I] of the present invention is not limited thereto.

Process 1

The compound represented by the general formula [I] can be prepared by reacting a compound represented by the general formula [II]:

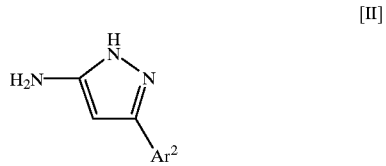

wherein $Ar^2$ is as defined above, with a carboxylic acid represented by the general formula [III]:

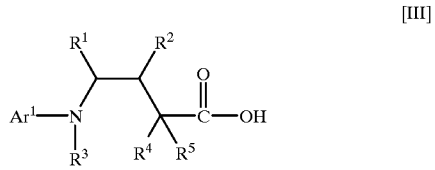

wherein $Ar^1$, $R^1$, $R^2$, $R^3$, $R^4$ and $R^5$ are as defined above, or its reactive derivative.

The reaction of the compound of the general formula [II] with the carboxylic acid of the general formula [III] is generally carried out using 0.5 mole to excess moles, preferably 1 mole to 1.5 moles, of the carboxylic acid of the general formula [III] with respect to 1 mole of the compound of the general formula [II].

The reaction is generally carried out in an inert solvent, and preferred examples of said inert solvent include methylene chloride, chloroform, tetrahydrofuran, dimethylformamide and pyridine and a mixture thereof.

Also, it is desirable to carry out the reaction in the presence of a condensing agent, and examples of said condensing agent to be used include N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)-phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoric acid azide and 1,1'-carbonyldiimidazole.

Said condensing agent can be generally used in an amount of from 1 mole to excess moles, preferably from 1 mole to 1.5 moles, with respect to 1 mole of the compound of the general formula [II].

The reaction temperature is generally within the range of from −50° C. to 100° C., preferably from −20° C. to 50° C.

The reaction time is generally within the range of from 30 minutes to 7 days, preferably from 1 hour to 24 hours.

The compound of the general formula [I] can also be prepared by reacting a reactive derivative of the carboxylic acid represented by the general formula [III], in stead of said carboxylic acid represented by the general formula [III], with the compound of the general formula [II].

As the reactive derivative of the carboxylic acid represented by the general formula [III], an acid halide, a mixed acid anhydride, an active ester, an active amide or the like may be used.

An acid halide of the carboxylic acid of the general formula [III] can be obtained by reacting the carboxylic acid of the general formula [III] with a halogenation agent according to any conventional method. Examples of the halogenation agent to be used include thionyl chloride, phosphorus trichloride, phosphorus pentachloride, phosphorus oxychloride, phosphorus tribromide, oxalyl chloride and phosgene.

A mixed acid anhydride of the carboxylic acid of the general formula [III] can be obtained by reacting the carboxylic acid of the general formula [III] with an alkyl chlorocarbonate such as ethyl chlorocarbonate or an aliphatic carboxylic acid chloride such as pivaloyl chloride according to any conventional method.

An active ester of the carboxylic acid of the general formula [III] can be obtained by reacting the carboxylic acid of the general formula [III] with an N-hydroxy compound such as N-hydroxysuccinimide, N-hydroxyphthalimide or 1-hydroxybenzotriazole; or a phenol compound such as 4-nitrophenol, 2,4-dinitrophenol, 2,4,5-trichlorophenol or pentachlorophenol, in the presence of a condensing agent such as N,N'-dicyclohexylcarbodiimide or 1-(3-dimethylaminopropyl)-3-ethylcarbodiimide according to any conventional method.

An active amide of the carboxylic acid of the general formula [III] can be obtained by reacting the carboxylic acid of the general formula [III] with 1,1'-carbonyldiimidazole or 1,1'-carbonylbis(2-methylimidazole) according to any conventional method.

The reaction of the compound of the general formula [II] with the reactive derivative of the carboxylic acid of the general formula [III] is generally carried out using 0.5 mole to excess moles, preferably 1 mole to 1.5 moles, of the reactive derivative of the carboxylic acid of the general formula [III] with respect to 1 mole of the compound of the general formula [II].

The reaction is generally carried out in an inert solvent, and preferred examples of said inert solvent include methylene chloride, chloroform, tetrahydrofuran, dimethylformamide and pyridine and a mixture thereof.

Though the aforementioned reaction proceeds in the absence of a base, it is desirable to proceed the reaction in the presence of any base in order to proceed the reaction more smoothly.

Examples of said base to be used include an organic base such as triethylamine, diisopropylethylamine, pyridine or 4-dimethylaminopyridine, or an inorganic base such as sodium hydroxide, potassium hydroxide, sodium carbonate, potassium carbonate or sodium bicarbonate.

It is desirable to use said base generally in an amount of from 1 mole to excess moles with respect to 1 mole of the compound of the general formula [II]. When said base is liquid, it can be used as both a solvent and a base.

The reaction temperature is generally within the range of from −50° C. to 100° C., preferably from −20° C. to 50° C.

The reaction time is generally within the range of from 5 minutes to 7 days, preferably from 30 minutes to 24 hours.

In the reaction of the compound of the general formula [II] with the carboxylic acid of the general formula [III] or its reactive derivative, a compound represented by the general formula [IV] or [V]:

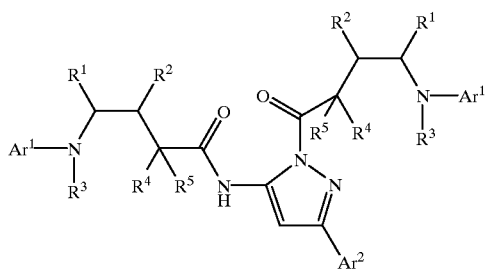

[IV]

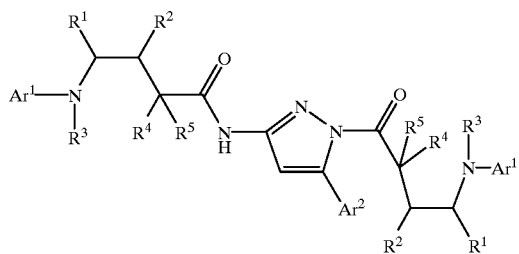

[V]

wherein $Ar^1$, $Ar^2$, $R^1$, $R^2$, $R^3$, $R^4$ and $R^5$ are as above, may be obtained as a by-product depending on the reaction conditions. Each of these compounds can be converted into the compound of the general formula [I] by hydrolyzing it in the presence of sodium hydroxide or potassium hydroxide or the like.

Process 2

A compound represented by the general formula [I-1]:

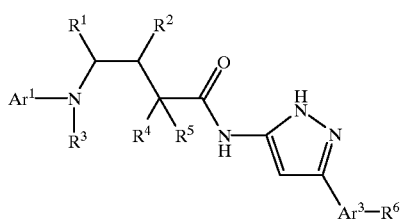

[I-1]

wherein $Ar^3$ represents an aryl or heteroaryl group which may have a substituent selected from the group consisting of lower alkyl, lower alkenyl, lower haloalkyl, lower alkoxy, lower alkylthio, lower alkylamino, lower dialkylamino and aryl groups; $R^6$ represents a lower alkyl, lower alkenyl or aryl group; and $Ar^1$, $R^1$, $R^2$, $R^3$, $R^4$ and $R^5$ are as defined above, can be prepared by reacting a compound represented by the general formula [VI]:

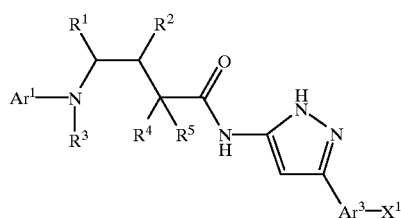

[VI]

wherein $X^1$ represents a halogen atom or a trifluoromethane-sulfonyloxy group; and $Ar^1$, $Ar^3$, $R^1$, $R^2$, $R^3$, $R^4$ and $R^5$ are as defined above, with a compound represented by the general formula [VII]:

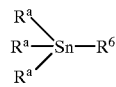

[VII]

wherein $R^a$ represents a lower alkyl group and $R^6$ is as defined above, in the presence of a palladium catalyst.

The reaction of the compound of the general formula [VI] with the compound of the general formula [VII] is generally carried out using 0.5 mole to 10 moles, preferably 1 mole to 3 moles, of the compound of the general formula [VII] with respect to 1 mole of the compound of the general formula [VI].

The reaction is generally carried out in an inert solvent, and preferred examples of said inert solvent include benzene, toluene, tetrahydrofuran, dimethylformamide and N-methylpyrrolidone and a mixture thereof.

Examples of the palladium catalyst to be used include tetrakis(triphenylphosphine)palladium, bis(triphenylphosphine)-palladium chloride, palladium acetate and tris(benzylideneacetone)dipalladium.

Said palladium catalyst is generally used in an amount of from 0.001 mole to 1 mole, preferably from 0.01 mole to 0.1 mole, with respect to 1 mole of the compound of the general formula [VI].

In addition, it is possible to add a phosphine ligand such as triphenylphosphine or tri-2-furylphosphine, or lithium chloride to the reaction system in order to proceed the reaction more smoothly.

The reaction temperature is generally within the range of from room temperature to 200° C., preferably from 60° C. to 150° C.

The reaction time is generally within the range of from 30 minutes to 7 days, preferably from 1 hour to 24 hours.

Process 3

A compound represented by the general formula [I-3]:

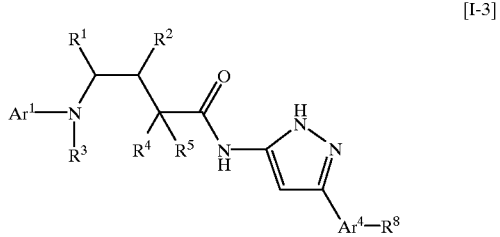

[I-3]

wherein $Ar^1$ represents an aryl or heteroaryl group which may have a substituent selected from the group consisting of a halogen atom and lower alkyl, lower haloalkyl, lower alkoxy, lower alkylthio, lower alkylamino, lower dialkylamino and aryl groups; $R^8$ represents a lower alkyl group; and $Ar^1$, $R^1$, $R^2$, $R^3$, $R^4$ and $R^5$ are as defined above, can be prepared by catalytically hydrogenating a compound represented by the general formula [I-2]:

[I-2]

wherein $R^7$ represents a lower alkenyl group; and $Ar^1$, $Ar^4$, $R^1$, $R^2$, $R^3$, $R^4$ and $R^5$ are as defined above, in the presence of a catalyst.

The reaction is generally carried out in an inert solvent, and preferred examples of said inert solvent include methanol, ethanol, methylene chloride, chloroform, tetrahydrofuran, dimethylformamide and acetic acid and a mixture thereof.

As the catalyst to be used in the reaction, a palladium-carbon catalyst or the like is desirable.

The reaction is generally carried out at room temperature.

The hydrogen pressure is generally from 1 to 50 atmospheric pressure, preferably from 1 to 5 atmospheric pressure.

The reaction time is generally within the range of from 30 minutes to 7 days, preferably from 1 hour to 24 hours.

The compound of the general formula [I], [I-1] or [I-3] can be easily isolated and purified by any conventional separation methods. Examples of such methods include solvent extraction, recrystallization, column chromatography and preparative thin layer chromatography.

These compounds can be converted into their pharmaceutically acceptable salts according to any conventional method and vice versa.

The compound of the general formula [II] to be used in the present invention is commercially available, or it can be prepared, for example, in accordance with the methods described in references such as Comprehensive Heterocyclic Chemistry, vol.5, edited by A. R. Katritzky, Pergamon Press (1984), or their modifications, or alternatively with the following process or the method as described in the reference examples.

wherein $X^2$ represents a halogen atom; and $Ar^2$ and $R^a$ are as defined above.

According to this process, the compound of the general formula [II] can be prepared by reacting a compound represented by the general formula (1) with acetonitrile in the presence of a base to obtain a compound represented by the general formula (3), and subsequently reacting said compound (3) with hydrazine.

Conditions for the reaction of the compound (1) with acetonitrile vary depending on the nature of the base to be used.

For example, when n-butyllithium, lithium diisopropylamide or the like is used as said base, the reaction is generally carried out in an inert solvent such as tetrahydrofuran or ethyl ether at a temperature of from −78° C. to room temperature for a reaction period of from 30 minutes to 6 hours.

When sodium hydride or the like is used as said base, the reaction is generally carried out in an inert solvent such as tetrahydrofuran, ethyl ether or dimethylformamide at a temperature of from room temperature to 100° C. for a reaction period of from 1 hour to 6 hours.

The reaction of the compound (3) with hydrazine is generally carried out in an inert solvent such as ethanol, propanol, isoamyl alcohol, acetic acid, benzene, toluene or xylene or a mixture, using hydrazine in an amount of from 0.5 mole to 10 moles, preferably from 1 mole to 1.5 moles, with respect to 1 mole of the compound (3).

The reaction temperature is generally from room temperature to boiling point of the solvent used, preferably from 50° C. to boiling point of the solvent used.

The reaction time is generally from 30 minutes to 7 days, preferably from 1 hour to 48 hours.

The hydrazine to be used in the reaction may be either anhydride or hydrate.

In addition, the compound of the general formula (3) can also be prepared by using a compound represented by the general formula (2) in stead of the compound represented by the general formula (1), and reacting it with a cyanide.

In this connection, the compound represented by the general formula (1) or (2) is commercially available or it can be prepared in accordance with known methods or their modifications which may be suitably combined if necessary.

The compound represented by the general formula [III] to be used in the present invention is commercially available or it can be prepared according to known methods or their modifications which may be suitably combined if necessary.

The compound represented by the general formula [VI] to be used in the present invention can be prepared using a material corresponding to the desired compound according to the process for the preparation of the compound of the general formula [II], modifications of Process 1, and known methods which may be suitably combined if necessary.

The compound represented by the general formula [VII] to be used in the present invention is commercially available or it can be prepared according to known methods or their modifications which may be suitably combined if necessary.

The usefulness of the compound of the present invention as a medicine is demonstrated by showing its antagonistic activity to NPY in the following pharmacological test examples.

PHARMACOLOGICAL TEST EXAMPLE 1
(test of inhibition of NPY binding)

cDNA Sequence encoding a human NPY Y5 receptor [International Publication Wo 96/16542] was cloned into expression vectors pcDNA3, pRc/RSV (manufactured by Invitrogen) and pCI-neo (manufactured by Promega). Using the cationic lipid method [see Proceedings of the National Academy of Science of the United States of America, vol.84, p.7413 (1987)], host cells COS-7, CHO and LM(tk-) (American Type Culture Collection) were transfected with the thus prepared expression vectors to obtain cells in which the NPY Y5 receptor had been expressed.

Each of the membrane preparations thus prepared from the cells in which the NPY Y5 receptor had been expressed was incubated together with each compound to be tested and 20,000 cpm of [$^{125}$I] peptide YY (manufactured by Amersham) at 25° C. for 2 hours in an assay buffer solution (25 mM HEPES buffer, pH 7.4, containing 10 mM magnesium chloride, 1 mM phenylmethylsulfonyl fluoride and 0.1% bacitracin) and then, the reaction mixture was filtered through a glass filter GF/C. After washing with 50 mM Tris buffer, pH 7.4, containing 0.3% BSA, radioactivity on the glass filter was measured using a gamma counter. Nonspecific binding was measured in the presence of 1 $\mu$M of peptide YY to calculate a concentration of each compound tested which is needed to inhibit 50% of the specific binding of the peptide YY (IC$_{50}$ value) [see Endocrinology, vol.131, p.2090 (1992)]. As the result, IC$_{50}$ value of the compound of Example 4 was calculated to be 39 nM.

As shown in the above, the compound of the present invention strongly inhibited the binding of the peptide YY (a homologue of NPY) to the NPY Y5 receptor.

PHARMACOLOGICAL TEST EXAMPLE 2
(test of inhibition of feeding behavior induced by bPP)

Under pentobarbital anesthesia (single intraperitoneal injection of 50 mg/kg), a chronic guide cannula (outer diameter 0.8 mm; inner diameter 0.5 mm; length 10 mm) was stereotactically inserted in a right lateral cerebral ventricle of each of SD male rats (7 to 8-week-old, 200 to 300 g) and fixed using a dental resin. A tip of the guide cannula was positioned 0.9 mm behind a bregma, 1.2 mm at the right of a median line and in the depth of 1.5 mm from the brain surface. An inner needle was inserted such that its tip projected from the tip of the guide cannula by about 2 mm and arrived to a lateral cerebral ventricle. After a recovery period of about one week, a bovine pancreatic polypeptide (bpp, 5 $\mu$g/head/10 $\mu$l) was administered to the lateral cerrebral ventricle. A compound to be tested was simultaneously administered as a mixture with bPP. Food intake during 2 hours from the administration was measured. In this connection, both bPP and the compound to be tested were administered after dissolving them in 50% propylene glycol.

The compound of the present invention significantly inhibits the increase in food intake induced by bPP (a homologue of NPY) simultaneously administered.

In consequence, the compound [I] of the present invention is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma, especially bulimia, obesity and diabetes.

The compound represented by the general formula [I] can be administered orally or parenterally and by formulating into any dosage forms suitable for such an administration, it can be used as an agent for the treatment of the diseases of circulatory organs such as hypertension, nephropathy, cardiopathy and angiospasm, the diseases of central nervous system such as bulimia, depression, epilepsy and dementia, the metabolic diseases such as obesity, diabetes and dysendocrisiasis, or glaucoma. In clinical use of the compound of the present invention, it is also possible to administer the compound after formulating into various dosage forms by adding any pharmaceutically acceptable additive (s). Examples of such additive include those which are generally used in the field of pharmaceutical preparations such as gelatin, lactose, sucrose, titanium oxide, starch, crystalline cellulose, hydroxypropylmethyl cellulose, carboxymethyl cellulose, corn starch, microcrystalline wax, white soft paraffine, magnesium aluminate methasilicate, anhydrous calcium phosphate, citric acid, trisodium citrate, hydroxypropyl cellulose, sorbitol, sorbitan fatty acid ester, polysorbate, sucrose fatty acid ester, polyoxyethylene hydrogenated castor oil, polyvinyl pyrrolidone, magnesium stearate, light anhydrous silicic acid, talc, vegetable oil, benzyl alcohol, gum arabic, propylene glycol, polyalkylene glycol, cyclodextrin and hydroxypropyl cyclodextrin.

Examples of the dosage form to be formulated as a mixture with these additives include solid preparations such as tablet, capsule, granule, powder or suppository; and liquid preparations such as syrup, elixir or injection, which can be prepared in accordance with any conventional method in the field of pharmaceuticals. In this connection, in the case of the liquid preparation, it may be in a form which is dissolved or suspended in water or other suitable solvent when used. Also, particularly in the case of an injection, it may be dissolved or suspended in physiological saline or glucose solution if necessary or further mixed with buffer and/or preservative.

The pharmaceutical preparation may contain the compound of the present invention in an amount of from 1.0 to 100% by weight, preferably from 1.0 to 60% by weight, with respect to the total preparation. The pharmaceutical preparation may also contain any other therapeutically effective compounds.

When the compound of the present invention is, for example, clinically used, its dosage and the number of times of its administration vary depending on the sex, age, body weight and the conditions of each patient and the nature and ranges of the intended therapeutic effects and the like. When it is administered to an adult, it is desirable in general to orally administer in an amount of from 0.1 to 100 mg/kg per day by dividing the daily dose into 1 to several times per day, or to parenterally administer in an amount of from 0.001 to 10 mg/kg by dividing the daily dose into 1 to several times per day.

BEST MODE FOR CARRYING OUT THE INVENTION

The present invention is described further in detail with reference to the following examples, but the invention should in no way be restricted thereby.

EXAMPLE 1

Preparation of 5-(4-chlorophenyl)-3-(1-phenylpiperidin-4-yl)-carbonylaminopyrazole 3-Amino-5-(4-chlorophenyl)pyrazole (23 mg) and 1-phenylpiperidine-4-carboxylic acid hydrochloride (28 mg) were dissolved in pyridine (5 ml) to which was subsequently added 1-(3-dimethylaminopropyl)-3-ethylcarbodiimide hydrochloride (35 mg), and the mixture was stirred overnight at room temperature. The reaction solution was diluted with ethyl acetate (30 ml), washed with water (30 ml), saturated aqueous sodium bicarbonate (30 ml) and saturated brine (30 ml) and then dried over anhydrous magnesium sulfate. Then, the solvent was distilled away. The resulting residue was crystallized from ethyl ether to obtain the title compound (20 mg) as white crystals (melting point: 209–211° C.).

Each of compounds of Examples 2 to 4 was obtained in the same manner as that described in Example 1 except that the starting materials used in Example 1 were replaced with appropriate starting material corresponding to the desired compound.

EXAMPLE 2

5-(4-methoxyphenyl)-3-(1-phenylpiperidin-4-yl)carbonylaminopyrazole melting point: 229–231° C.

EXAMPLE 3

5-(3,4-dichlorophenyl)-3-(1-phenylpiperidin-4-yl)carbonylaminopyrazole melting point: 126–129° C.

EXAMPLE 4

3-[1-(3-chlorophenyl)piperidin-4-yl]carbonylamino-5-(4-methoxyphenyl)pyrazole melting point: 92–102° C.

REFERENCE EXAMPLE

Preparation of 3-amino-5-(3,4-dichlorophenyl)pyrazole 3,4-Dichlorobenzoylacetonitrile (3.0 g) was dissolved in ethanol (15 ml) to which was subsequently added hydrazine monohydrate (0.67 ml) while cooling with ice. The mixture was heatedunder reflux for 5 hours and allowed to cool. Then, the solvent was distilled away under a reduced pressure. The resulting residue was recrystallized from ethyl acetate-hexane to obtain the title compound (1.72 g) as colorless crystals (melting point: 169–170° C.).

INDUSTRIAL APPLICABILITY

Since the compound of the present invention has an action of inhibiting NPY, it is useful as an agent for the treatment of various diseases associated with NPY, for example, diseases of circulatory organs such as hypertension, nephropathy, cardiopathy and angiospasm, diseases of central nervous system such as bulimia, depression, epilepsy and dememtia, metabolic diseases such as obesity, diabetes and dysendocrisiasis, or glaucoma.

What is claimed is:

1. A compound represented by the general formula [I]:

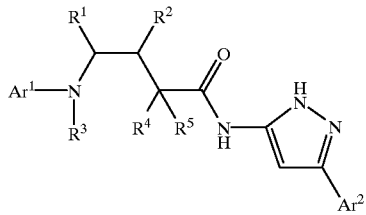

(I)

wherein $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ and $R^2$ may be the same or different and each represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which is unsubstituted or substituted with a lower alkyl group; and $R^5$ represents a hydrogen atom or a lower alkyl or lower alkoxy group, or a salt thereof.

2. The compound as claimed in claim 1 wherein the aryl group as $Ar^1$ or $Ar^2$ is a phenyl group.

3. The compound as claimed in claim 1 wherein each of $R^1$ and $R^2$ is a hydrogen atom.

4. The compound as claimed in claim 1 wherein $R^3$ and $R^4$ are linked to each other to form an alkylene group containing 2 to 4 carbon atoms which is unsubstituted or substituted with a lower alkyl group.

5. The compound as claimed in claim 4 wherein the alkylene group contains 2 carbon atoms.

6. The compound as claimed in claim 1 which is
   5-(4-chlorophenyl)-3-(1-phenylpiperidin-4-yl)carbonylaminopyrazole,
   5-(4-methoxyphenyl)-3-(1-phenylpiperidin-4-yl)carbonylaminopyrazole,
   5-(3,4-dichlorophenyl)-3-(1-phenylpiperidin-4-yl)carbonylaminopyrazole, or
   3-[1-(3-chlorophenyl)piperidin-4-yl]carbonylamino-5-(4-methoxyphenyl)pyrazole.

7. A process for the preparation of a compound represented by the general formula (I):

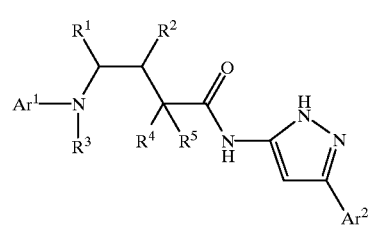

(I)

wherein $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ and $R^2$ may be the same or different and each represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which is unsubstituted or substituted with a lower alkyl group; and $R^5$ represents a hydrogen atom or a lower alkyl or lower alkoxy group, or a salt thereof which comprises reacting a compound represented by the general formula (II):

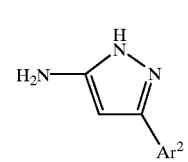

(II)

wherein $Ar^2$ is as defined above, with a carboxylic acid represented by the general formula [III]:

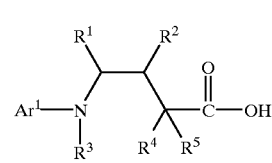

(III)

wherein $Ar^1$, $R^1$, $R^2$, $R^3$, $R^4$ and $R^5$ are as defined above, or its reactive derivative.

8. A neuropeptide Y receptor antagonist comprising a compound represented by the general formula (I):

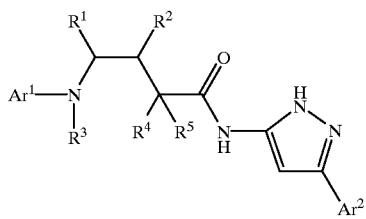

wherein $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ and $R^2$ may be the same or different and each represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which is unsubstituted or substituted with a lower alkyl group; and $R^5$ represents a hydrogen atom or a lower alkyl or lower alkoxy group, or a salt thereof as an active ingredient.

9. A pharmaceutical composition comprising a neuropeptide Y receptor antagonistic effective amount of a compound of formula (I) as set forth in claim 1 or a pharmaceutically acceptable salt thereof and at least one pharmaceutically acceptable adjuvant.

10. The composition of claim 9 comprising from about 1.0 to 60 percent by weight of the compound of formula (I) or a pharmaceutically acceptable salt thereof.

11. A method for the treatment of bulimia, obesity or diabetes comprising administering to a patient in need thereof, a neuropeptide Y receptor antagonistic effective amount of a compound of formula (I) as set forth in claim 1 or a pharmaceutically acceptable salt thereof.

* * * * *